United States Patent [19]

Ware et al.

[11] Patent Number: 5,139,792

[45] Date of Patent: Aug. 18, 1992

[54] METHOD AND SYSTEM FOR DISPENSING LIVE BACTERIA INTO ANIMAL FEED AND DRINKING WATER

[75] Inventors: Douglas R. Ware, Bothell; Richard E. Herman; Leslie A. Walter, both of Redmond, all of Wash.

[73] Assignee: Bio-Techniques Laboratories, Inc., Redmond, Wash.

[21] Appl. No.: 555,910

[22] Filed: Jul. 19, 1990

[51] Int. Cl.$^5$ .............................................. A23K 1/00
[52] U.S. Cl. ........................................ 426/2; 426/61; 426/807
[58] Field of Search .................. 426/2, 61, 807

[56] References Cited

U.S. PATENT DOCUMENTS

| | | |
|---|---|---|
| 3,932,670 | 1/1976 | Sakurai . |
| 3,953,609 | 4/1976 | Farr . |
| 3,984,575 | 10/1976 | Farr . |
| 4,518,696 | 5/1985 | Gehrman et al. . |
| 4,657,762 | 4/1987 | Mikkola et al. . |
| 4,689,226 | 8/1987 | Nurmi et al. . |
| 4,815,042 | 3/1989 | Pratt . |
| 4,839,281 | 6/1989 | Gorbach et al. . |
| 4,889,433 | 12/1989 | Pratt . |
| 4,910,024 | 3/1990 | Pratt . |

OTHER PUBLICATIONS

Klaenhammer, T. R., "Our industry today: Microbiological considerations in Selection and Preparation of Lactobacillus Strains for Use as Dietary Adjuncts," *J. Dairy Sci.* 65(7):1339–1349, 1982.

Product information: Cobactin TM, DR Microbial Gastro-Intestinal Stabilizer, Bio-Techniques Laboratories, Inc., Redmond, Wash.

Product information: A commercially available apparatus sold under The Liquid Spray trademark by Liquid Systems, Inc., Greenville, S.C.

*Primary Examiner*—R. B. Penland
*Attorney, Agent, or Firm*—Christensen, O'Connor, Johnson & Kindness

[57] ABSTRACT

A method for preparing, at an animal feedlot, a suspension of microaerophilic or anaerobic bacteria at a known, accurate concentration in anticipation of dispensing the suspension of bacteria into animal feed or drinking water. The method allows the livestock feedlot or poultry operators to maintain the suspension of bacteria in a substantially viable condition without significant loss of viability and without requiring constant or intermittent agitation after the suspension is created. Refrigeration of the suspension is also unnecessary if the suspension of bacteria is dispensed within a predetermined period of time after preparation.

25 Claims, 1 Drawing Sheet

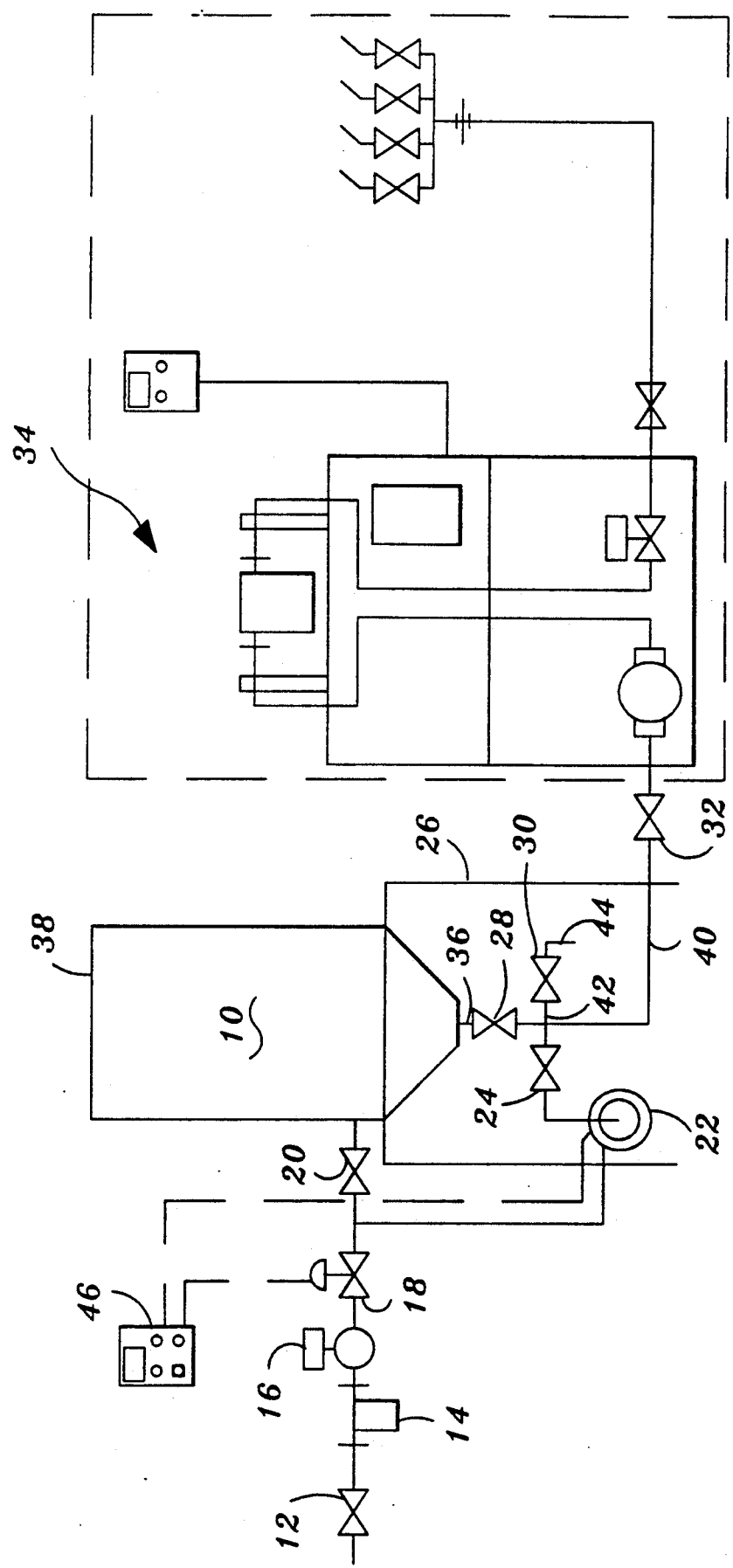

METHOD AND SYSTEM FOR DISPENSING LIVE BACTERIA INTO ANIMAL FEED AND DRINKING WATER

FIELD OF THE INVENTION

The present invention relates to animal husbandry, and particularly to methods and systems for providing live bacteria as feed supplements to livestock and poultry. More particularly, the invention provides a method and system for dispensing predetermined doses of live bacteria, without agitation or refrigeration, at animal feedlots while avoiding bacterial mortality and other problems associated with prior feedlot delivery techniques.

BACKGROUND OF THE INVENTION

It has long been a common practice to administer chemical additives to cattle and other livestock to supplement feed rations, thereby providing a balanced diet, protecting the animals from disease, and stimulating growth. For example, administration of certain live bacteria, such as lactobacilli, can help restore optimal intestinal flora in animals such as cattle, especially after stressful situations such as transport to a feedlot. With regular administration, the lactobacilli may increase nutrient absorption efficiency and help control the proliferation of harmful microorganisms in animals' digestive tracts that could otherwise cause disease conditions that adversely affect rates of animal development and weight gain. Most commonly administered to cattle for such purposes are strains of *Lactobacillus acidophilus*, a microaerophilic lactic acid producer. While lactobacilli have been effective for promoting animal health, they suffer from physiological properties that make their storage and handling problematic.

Concentrated cultures composed of single or mixed strains of lactic acid bacteria have been prepared under batch fermenter conditions, concentrated to a smaller volume, and then placed in frozen or dried storage. However, the lactobacilli reportedly do not respond well to lyophilization, spray drying, or conventional frozen storage at −20° C. Therefore, liquid nitrogen and ultra-cold freezers (−80° to −100° C.) have been preferred methods for maintaining the highest culture viability and activity. See: Klaenhammer, T. R., Our industry today, *J. Dairy Sci.* 65: 1339-1349, 1982.

For example, in the manufacture of a bacterial preparation for the prophylaxis of intestinal disturbances in poultry, the cultivated lactobacilli are deep-frozen (−70° C.) or lyophilized; see U.S. Pat. No. 4,689,226 (column 4, line 64). Lactobacillus strains for human therapy are often provided in lyophilized form; see U.S. Pat. No. 4,839,281 (column 5, line 52).

U.S. Pat. No. 4,518,696 (Gehrman et al.) reports that dried, stabilized concentrates of *Lactobacillus acidophilus* have been administered to mammals in milk and other aqueous suspensions. Unless the suspension is to be stored and distributed under refrigerated conditions, such as with commercial acidophilus milk, it has reportedly heretofore been necessary to prepare the suspension immediately prior to use in order to be certain that a sufficiently high percentage of the cells administered remain viable at the time of administration. Lyophilized concentrates of lactobacilli have been prepared, but such dried cell concentrates are reportedly not adequately stable in aqueous suspension unless the suspension is refrigerated. The patent discloses the use of sunflower seed oil as a liquid suspending medium for dry lactobacilli, resulting in a slow suspension manifesting a high degree of cell stability at room temperature.

A commercially available lactobacillus feed additive concentrate for cattle, sold under the COBACTIN ® trademark by Bio-Techniques Laboratories, Inc., Redmond, Wash., is a lyophilized material. The accompanying directions recommend mixing the lyophilized contents into cool water and keeping the liquid concentrate cool. The liquid concentrate is diluted in cool water and sprayed over livestock feed. If the liquid concentrate is not used immediately, it can reportedly be refrigerated for up to 10 days to prolong viability.

U.S. Pat. No. 4,910,024 (Pratt) in particular, describes a method and apparatus for administering live bacteria such as lactobacilli as feed additives to livestock and poultry. This patent reports that lyophilizing the bacteria greatly extends the shelf life of commercially packaged bacteria formulations; however, such packaging still does not solve the problem of maintaining the bacteria in a live state and delivering them to large numbers of animals in proper dosages after the package is opened. Without some means of extending viability, bacteria from an unopened package must reportedly be properly diluted and presented to the animals within a very short time after opening the package, which is time-prohibitive and impractical in large feedlots. To overcome these difficulties, the lyophilized bacteria are suspended in an aqueous medium at a temperature (generally between 36° to 50° F.) that is maintained sufficiently low to reportedly inhibit anabolic or catabolic processes that reduce viability.

Lyophilized lactobacilli, such as the type used in Pratt, are typically stored in a suitable dry carrier including a flow agent such as sugar, and cryoprotectants such as monosodium glutamate and nonfat milk solids. These diluents add a significant amount of solids to the packaged concentrate. The significant amount of solids associated with the lyophilized bacteria makes it difficult, if not impossible, to maintain a homogenous suspension of the concentrate without constant or intermittent agitation, because the solids settle out of the suspension. Settling of the solids is undesirable because the sediment clogs delivery and transport lines, which must then be cleaned frequently. A uniform suspension of bacteria is necessary to ensure that the doses that are delivered to the livestock contain predictable and consistent cell counts. As reported in Pratt, without constant or intermittent agitation, the suspensions can become nonuniform in as little as 15 minutes.

Furthermore, lyophilization is a harsh process for the bacteria cells to survive, often resulting in a 40% to 60% loss of viability. Another disadvantage of lyophilization is that the process is energy-intensive. The costs of the energy contribute to the overall cost of the lyophilized bacteria.

SUMMARY OF THE INVENTION

The present invention provides a superior method for dispensing live bacteria into the feed or water rations of animals such as livestock and poultry. A frozen concentrate of live bacteria is introduced into cool or tepid water to prepare a suspension of the concentrate in the water. The frozen concentrate does not include flow agents such as sugar, or cryoprotectants such as monosodium glutamate or nonfat milk solids. A uniform suspension of the concentrate can consequently be maintained, without further mixing or agitation, for the 12- to 24-hour period that is typically required for feedlot applications. Several direct advantages result. First, mortality of bacteria from shear forces associated with agitation of the solution is virtually eliminated. Second, for microaerophilic bacteria such as lactobacilli and anaerobic bacteria, mortality of the bacteria due to exposure to oxygen introduced by the agitation is greatly curtailed.

Several other auxiliary advantages result from not introducing sugar and cryoprotectants into the suspension. First, delivery lines, measuring devices, and particularly spray nozzles do not become clogged or caked with such suspended solids or the suspended solids after they settle out of the suspension. Reducing clogging and caking reduces the likelihood that inaccurate measuring and dispensing will occur, and reduces system malfunction time. Second, the suspension contains significantly reduced amounts of nutrients that can support the growth of undesirable microorganisms such as yeast.

These advantages are possible because applicants have surprisingly found that lactobacilli remain viable in solution at ambient temperatures (i.e., without refrigeration) for the time periods required for feedlot applications, and furthermore, that refrigeration is nonetheless required when lyophilized cultures are used.

In a preferred embodiment, as shown and described, a desired volume of a frozen concentrate of bacteria is suspended in a vessel. A water meter, scale, or other volumetric measuring means monitors the volume of the liquid contents in the vessel and ensures that the vessel is filled precisely with a preselected volume of an aqueous medium, typically water. The bacteria in the vessel is dispersed and suspended in the aqueous medium by a recirculation pump. After the bacteria are uniformly dispersed and suspended within the aqueous medium, recirculation of the mixture is discontinued. The steps of the method can be controlled by an electronic control means. The vessel is covered to prevent environmental contamination of the contents and to restrict air circulation. The cover is removable to allow filling of the vessel with the aqueous medium and for adding a fresh supply of the frozen concentrate of bacteria. The apparatus also includes a means for controllably delivering a predetermined volume or aliquot of the suspension of bacteria from the vessel for application to livestock feed or drinking water, either directly or by first intermixing with other additives, such as microingredient feed additives or liquid diluents.

In another aspect, the invention provides a package containing a frozen concentrate comprising live bacteria, in association with a protocol for introducing the frozen concentrate into an aqueous medium to prepare a suspension of the bacteria in the aqueous medium and maintain the suspension without agitation and without refrigeration for at least about 30 minutes while dispensing aliquots of the suspension into animal feed or drinking water.

BRIEF DESCRIPTION OF THE DRAWINGS

The above and other objects and advantages of the present invention will become more apparent from the following FIGURE and detailed description of a preferred embodiment, wherein FIGURE is a block diagram schematically illustrating a representative apparatus for dispensing uniform doses of live bacteria at livestock feedlots without refrigeration or agitation over extended periods of 48 hours or more.

DETAILED DESCRIPTION OF THE INVENTION

The present invention provides a method for preparing and storing a suspension of live microaerophilic and anaerobic bacteria in an aqueous medium for dispensing in predetermined dosages to animal feed or drinking water on a continuous basis, for example at a feedlot. Microaerophilic bacteria are generally tolerant of small amounts of oxygen and may even require small amounts to remain viable. Lactobacilli is a microaerophilic bacteria. Anaerobic bacteria generally do not require oxygen to survive and in some instances may be intolerant of oxygen. As used herein, the term "livestock" refers to animals kept or raised for use or pleasure, including but not limited to, beef cattle and milk cows. In a preferred embodiment, a frozen concentrate of bacteria is thawed and then suspended in an aqueous medium having minimal nutrient content to prevent growth or multiplication of the bacteria while still sustaining viability of the organisms. The bacteria are suspended in the aqueous medium during or immediately after their addition to the aqueous medium. Once the bacteria are suspended in the aqueous medium, no further agitation or recirculation is necessary to maintain the suspension. The concentration of the bacteria in the suspension is preferably such that it can be applied directly to feed rations or drinking water for the livestock.

Surprisingly, applicants have found that a preferred bacteria, *Lactobacillus acidophilus*, remains viable in solution at ambient temperature over periods required for feedlot applications. Accordingly, one advantage of the present method is that the suspension of bacteria does not require refrigeration in order to maintain the viability of the bacteria for extended periods of time on the order of 48 hours or more.

Another surprising finding by applicants is the ability to maintain a suspension of bacteria from a frozen concentrate without constant or intermittent agitation. Though not intending to be limited to the following explanation, it is believed that the ability to maintain the suspension without agitation is made possible by the absence of dry carriers for the bacteria, such as sugar and cryoprotectants. If present, the solids will settle out of the suspension. Since the solids can bind the bacteria in suspension, as the solids settle out of suspension, the uniformity of the concentration of the bacteria in suspension decreases.

A preferred bacterium is *Lactobacillus acidophilus* strain BT 1386, which has been deposited under Accession No. 53545 at the American Type Culture Collection, 12301 Parklawn Drive, Rockville, Md.

The lactobacilli can be cultivated by a known technique that involves inoculating a growth medium with a mother culture of the desired lactobacilli. The lactobacilli cells are grown up by fermenting the medium and then harvested by concentrating the fermented medium.

A representative method of concentrating the cells grown up in the fermentation process uses a continuous centrifuge that causes almost 9,000 g's to be exerted on the cells. The centrifugation is preferably continued until approximately 90 to 95% of the cells are recovered. Other methods of concentrating the cells can be used so long as they provide the desired degree of concentration and do not destroy an excessive number of live cells.

The cell concentrate can be collected continuously from the centrifuge. After collection, the cell concentrate should be refrigerated, for example, by placing a vessel carrying the collected concentrate in an ice bath. Depending on the length of time over which the concentrate is collected, the cell concentrate can be collected in one container and periodically transferred to another container sitting in an ice bath.

Once the centrifuging step is complete or a predetermined amount of cell concentrate has been collected, the concentrate is prepared for freezing. A representative method for freezing the concentrate first adjusts the pH of the concentrate to about 6.4 to 6.5. The pH can be adjusted by adding potassium hydroxide or another basic compound that is not lethal to the bacteria. In this representative embodiment, the cell concentrate is then dispensed into suitable individual containers, for example, metal cans. The concentrate is then frozen as quickly as possible, for example, using liquid nitrogen or a less expensive alcohol and dry ice bath. Preferably, the mode of freezing should freeze the concentrate within about 10 minutes. After the concentrate is frozen, it can be stored at sub-zero temperatures, for example $-20°$ F.

The frozen concentrate does not include cryoprotectants that are typically added as powders to a collected cell concentrate just prior to lyophilization of the concentrate or carrier solids that are added to the lyophilized cell concentrate after lyophilization. Accordingly, a packaged frozen concentrate has a solids-to-live bacteria ratio less than the solids-to-live bacteria ratio of a packaged lyophilized culture. For example, the frozen concentrate contains about 7.5 grams of solids per 10,000 doses of live bacteria (approximately $5 \times 10^{12}$ colony forming units, CFU) for cattle. The majority of the weight of the frozen concentrate is attributable to water. For example, an amount of frozen concentrate adequate to provide the 10,000 doses of bacteria described above would include approximately 67.5 grams of water. In contrast, a lyophilized culture contains about 100 grams of solids per 10,000 doses of live bacteria (approximately $5 \times 10^{12}$ CFU) for cattle.

The frozen concentrate of bacteria can be directly deposited into a volume of the aqueous medium or it can be thawed first and then added to the aqueous medium. For example, about 75 grams of a frozen concentrate of bacteria added to approximately 10 to 25 gallons of water yields a quantity of bacteria in suspension sufficient to dose 10,000 head of cattle at a single feeding. For beef cattle, the concentration of the cells per dose should be at least about $5 \times 10^8$ CFU per dose. For dairy cows, the concentration should be even higher. For poultry, about 75 grams of the frozen concentrate of bacteria added to approximately 7 gallons of water yields a quantity of bacteria in suspension sufficient to dose approximately 1,000,000 head of poultry at a single feeding.

The apparatus used to carry out a method in accordance with the present invention is locatable at a feedlot where batches of the suspension can be formulated and prepared in advance of dispensing the bacteria into livestock feed or drinking water. Referring to the FIGURE, such an apparatus includes a mixing vessel 10 in which a suspension of bacteria is prepared, stored, and maintained to be used as a daily supplement for livestock. Mixing vessel 10 has associated with it a number of peripheral components, including means for introducing controlled amounts of an aqueous medium into mixing vessel 10, such means includes an inlet water valve 12, a strainer 14, a water meter 16, a solenoid valve 18, and a recirculation valve 20; means for recirculating liquid through mixing vessel 10, such means includes a recirculation pump 22 and a pump valve 24; means for electronically controlling recirculation pump 22 and solenoid valve 18; and a support frame 26 for carrying mixing vessel 10. The apparatus used to carry out a method in accordance with the present invention can be used in conjunction with a delivery system, generally represented by reference numeral 34, for dispensing aliquots of the suspension of bacteria directly into feed rations or drinking water. The term "aliquots" as used herein refers to a fractional portion of the suspension containing a predetermined number of live bacteria, which fractional portions can be dispensed either continuously or intermittently from the vessel containing the suspension. Optionally, the apparatus can be used in conjunction with a delivery system that, in addition to dispensing aliquots of the suspension into feed or drinking water, also adds other microingredient feed additives to the aliquots before dispensing the aliquots. Another useful type of delivery system is one that receives and dilutes aliquots of the suspension before dispensing the aliquots into livestock feed or drinking water.

Although not shown, other peripheral components that can optionally be associated with mixing vessel 10 include a means for monitoring the temperature of the suspension in the mixing vessel, means for detecting the liquid level in the mixing vessel, or means for determining the weight of the contents in the mixing vessel.

Support frame 26 serves to support mixing vessel 10 in an upright position. If an optional weighing means or liquid detecting means is employed, such means may also be supported by support frame 26.

Mixing vessel 10 is cylindrical with its lower end shaped like an inverted cone to facilitate complete draining of fluids contained therein. Mixing vessel 10 is preferably constructed of stainless steel; however, it may be made from other suitable materials that do not corrode, contribute toxic substances to aqueous liquids that contact the material, or deteriorate from prolonged contact with aqueous solutions of the types anticipated during use. The material should also exhibit acceptable thermal and mechanical characteristics. The volume of mixing vessel 10 is preferably within the range of about 50.0 to 250.0 gallons, but may be smaller or larger depending on the size of the production unit and the desired volume of the aqueous medium to be added. More preferably, the volume of mixing vessel 10 is such that one quart to one gallon of volume is provided per ton of feed that is to be administered with bacteria from a single batch prepared in the vessel.

Mixing vessel 10 is mounted at the uppermost portion of support frame 26. The apex of the conical portion has an opening that is hydraulically connected to a vessel exit valve 28 through a pipe 36. The upper end of vessel 10 is covered with a horizontal panel or lid 38 that is hinged to allow access to the interior of mixing vessel 10. Access to the interior of mixing vessel 10 allows addition of a fresh supply of aqueous medium or of thawed cultures of bacteria, or for cleaning or inspecting the interior of mixing vessel 10.

Though not shown, mixing vessel 10 can be surrounded by means for thermally insulating the vessel. Such means can include foam or fiber insulation. The thermal insulating means is preferred in order to minimize temperature fluctuations of the aqueous medium.

The inlet port of vessel exit valve 28 is connected to the distal opening of pipe 36 opposite the opening in the bottom of mixing vessel 10. Vessel exit valve 28 and other valves described herein are preferably solenoid valves, but other types of electrically actuated valves can also be used. The outlet port of vessel exit valve 28 opposite the inlet port is connected via a conduit 40 to the inlet port of a delivery valve 32. The outlet port of delivery valve 32 is hydraulically connected to delivery system 34. Conduit 40 is also hydraulically connected to the inlet port of a discharge valve 30 through a pipe 42. The outlet port of discharge valve 30 opposite the inlet port is hydraulically connected to a discharge conduit 44.

Above its conical bottom, mixing vessel 10 is hydraulically connected to a source of an aqueous medium, such as clean water. Clean water enters mixing vessel 10 through inlet water valve 12. Inlet water valve 12 has its inlet port hydraulically connected to the water source (not shown) and its outlet port hydraulically connected to strainer 14. Strainer 14 is preferably a screen of 80 mesh and serves to remove particulate matter from the water. The outlet side of strainer 14 is hydraulically connected to water meter 16 that measures the mass or volume of water passing into mixing vessel 10. Downstream from water meter 16 is solenoid valve 18 that is controlled by an electronic control 46. The outlet side of solenoid valve 18 is hydraulically connected to the inlet port of recirculation valve 20. Intermediate the outlet port of solenoid valve 18 and the inlet port of recirculation valve 20 is a "tee" that hydraulically connects the conduit between solenoid valve 18 and recirculation valve 20 to the inlet port of recirculation pump 22. The outlet port of recirculation pump 22 is hydraulically connected to the inlet port of pump valve 24. The outlet port of pump valve 24 is hydraulically connected to conduit 40 intermediate the outlet port of vessel exit valve 28 and the inlet port of delivery valve 32. Recirculation pump 22 is also electrically connected to electronic control 46.

The suspension of the frozen concentrate in an aqueous medium is prepared in accordance with one embodiment as described below. Mixing vessel 10 is filled with an aqueous medium such as water or other suitable liquid by opening inlet water valve 12, solenoid valve 18, and recirculation valve 20. The aqueous medium has a minimal nutrient content to prevent growth or multiplication of the bacteria while still maintaining viability of the microorganisms. When mixing vessel 10 is being filled with the aqueous medium, vessel exit valve 28 is closed. Once water meter 16 indicates that the predetermined amount of water has been introduced into mixing vessel 10, inlet water valve 12 and solenoid valve 18 are closed. Alternatively, the aqueous medium can be introduced into mixing vessel 10 through lid 38.

In order to disperse and suspend the frozen concentrate of bacteria in the water contained within mixing vessel 10, discharge valve 30 and delivery valve 32 must be closed. Recirculation valve 20, pump valve 24, and vessel exit valve 28 must be opened and recirculation pump 22 energized, causing the water in mixing vessel 10 to circulate through the hydraulic loop that includes recirculation valve 20, recirculation pump 22, pump valve 24, vessel exit valve 28, and mixing vessel 10. The frozen cultures of bacteria can be added before or during operation of recirculation pump 22. The recirculation pump is operated until the bacteria is uniformly dispersed and suspended in the water in mixing vessel 10.

The temperature of the water that is introduced into mixing vessel 10 can range between about 33° F. and 100° F. Preferably, the water is at a temperature ranging between about 40° F. and 80° F. If the operation is being carried out under extremely arid and hot conditions, the water may be cooled prior to introduction into the mixing vessel. Preferably, refrigeration is not necessary after the water enters the mixing vessel.

The water that is introduced into the mixing vessel can include small amounts of other ingredients such as water soluble vitamins, trace minerals, amino acids, or water soluble antibiotics. For cattle, about 75 grams of the thawed frozen concentrate of bacteria is added to about 10 to 25 gallons of water. It has been found that the cell count per dose should be maintained at a level above about $5 \times 10^8$ cells per dose in order to have effective results for large livestock such as cattle.

In addition to water, other useful liquids for forming a suspension or dispersion of bacteria include milk, liquid molasses, and other liquids that are not detrimental to the viability of the bacteria.

Operating recirculation pump 22 at a flow rate of approximately 10 to 100 gallons per minute, and preferably about 50 gallons per minute for about two to ten minutes, preferably about five minutes provides a uniform suspension of the bacteria within the water. A satisfactory suspension of the bacteria within the water is evidenced qualitatively by uniform cloudiness of the suspension and a substantial absence of sedimentation. The uniformity of the suspension can also be qualitatively determined by adding a coloring agent such as food coloring and observing the uniformity of the color of the suspension. Quantitatively, the uniformity of the concentration of the bacteria in suspension can be evaluated by removing samples from several levels in the vessel and culturing for live cells of the pure bacterial culture. The respective cultures can be compared to determine the concentration of cells in each of the samples. A uniform suspension should provide samples from different locations in the vessel that have cell concentrations within about 10% to 20% of each other.

Recirculation should be carried out under conditions such that the period of time and degree of agitation is minimal in order to minimize the mortality of viable cells due to physical abuse or exposure to oxygen during the agitation. The effect of agitation and recirculation on the viability of a suspension of live, microaerophilic, or anaerobic bacteria is illustrated in Example 1 at the end of this description.

Once a uniform suspension has been achieved, the recirculation of the mixture is discontinued by disconnecting recirculation pump 22 from the power source, closing recirculation valve 20, pump valve 24, and vessel exit valve 28. Once the bacteria has been adequately suspended as described above, no further agitation is required in order to maintain the suspension for extended periods between preparation of the suspension and its dispensing to livestock feed or drinking water. It has been observed by applicants that once the bacteria are satisfactorily suspended within water, the suspension will maintain itself for periods on the order of about seven days. Accordingly, if the viability of the bacteria can be maintained, the suspension can be delivered up to seven days or more after it is formed.

Nonuniformity of the concentration of the bacteria in the suspension is undesirable because the doses administered from the suspension to the livestock will have nonuniform bacteria concentrations. In order to ensure that the suspension is uniform, the operator, just prior to dispensing the suspension of bacteria, should observe the suspension for uniform cloudiness or uniform coloring of the suspension.

Although refrigeration can be provided to the suspension in the mixing vessel, it has been found that refrigeration is unnecessary for periods of normal feedlot applications in order to maintain the viability of the bacteria in suspension, particularly when the suspension is to be administered within about 48 hours after its initial preparation.

When it is determined that the suspension of bacteria is to be dispensed, a predetermined amount of the suspension is removed from mixing vessel 10 by opening vessel exit valve 28 and delivery valve 32, which allows the suspension to be received by delivery system 34. Preferably, agitation or recirculation of the suspension in mixing vessel 10 is not provided during the dispensing of the suspension.

Delivery system 34 either dispenses the suspension directly to the livestock feed without adding other microingredients, or alternatively mixes the suspension with other microingredients or a liquid diluent such as water, prior to dispensing the mixture into livestock feed. The delivery system can also dispense the suspensions of bacteria to the livestock in other manners such as directly into the drinking water or to a drenching apparatus for direct oral administration of dosages to the animals. A commercially available system for delivering the suspension to the livestock or poultry without adding feed additives or liquid diluents is sold under the name THE LIQUID SPRAY, by Liquid Systems, Inc., Greenville, S.C. An example of a delivery system capable of measuring, dispensing, and delivering different combinations and proportions of microingredient feed additives concentrates into aliquots of the bacterial suspension is described in U.S. Pat. Nos. 4,815,042 and 4,889,433 to Pratt, the disclosures of which are expressly incorporated herein by reference.

In another embodiment, a concentrated suspension of bacteria can be formed and then introduced into a liquid carrier such as water, that dilutes the concentrate to a predetermined concentration consistent with its end use. An example of an apparatus for carrying out this type of operation is commercially available under the name DOSATRON® from Agri-Pro, Iowa Falls, Iowa.

The suspension should be dispensed into the livestock feed just before feeding to the livestock. As the suspension of bacteria is added to the livestock feed, the feed is tumbled or otherwise agitated to ensure uniform dispersion of the bacteria throughout the feed. Afterward, the feed is delivered to feed bunks for presentation to the animals.

The concentration and volume of the bacterial suspension contained in mixing vessel 10 can be carefully tailored to insure that the entire amount of feed to which the suspension of bacteria is added is uniformly coated with bacteria without wasting excess liquid. Further, the concentration of bacteria in the suspension can be carefully tailored to such variables as the total mass or volume of feed, average feed granule size, particle density, surface area, and amount of feed normally consumed by each animal at a single feeding, to optimize the dosage of bacteria each animal receives at feeding and obtain the desired rate of weight gain. The frequency of dispensing the suspension of bacteria into livestock feed and drinking water can also be optimized to achieve the desired health benefits.

A preferred embodiment provides the following advantages over processes that use lyophilized cultures of bacteria:

1. Stable, uniform suspensions can be formed and then maintained for extended periods without intermittent or continuous agitation or recirculation;

2. Viability of the bacteria in the effective range of concentration for enhancing animal health is preserved for extended periods without refrigeration;

3. Lower mortality of bacteria compared to existing agitated, recirculated, and refrigerated delivery systems;

4. Minimal solids required in the frozen concentrates decreases sanitation, measuring, dispensing, and maintenance problems; and 5. Frozen concentrates provided to the user contain a higher percentage of live healthy cells.

The following examples illustrate the adverse effect that agitation and recirculation have on the viability of *Lactobacillus acidophilus* BT 1386, the effect that temperature has on the viability of bacteria in an aqueous suspension, and the ability to maintain a suspension of bacteria from a frozen concentrate for extended periods of time. The examples are not intended to limit the scope of the present invention.

EXAMPLE 1

To compare the effects of different stirring conditions on the viability of freeze-dried *Lactobacillus acidophilus* BT 1386, several typical formulations were prepared separately, stored at 39° F., and subjected to either intermittent agitation, recirculation, or neither (static). A typical 10,000 dose formulation for cattle was prepared by rehydrating 100 grams of freeze-dried *Lactobacillus acidophilus* BT 1386 containing approximately $5\times10^{10}$ colony forming units per gram in 8 liters of tap water. This formulation achieves a bacterial cell count of about $6\times10^{8}$ colony forming units (CFU) per milliliter (ml).

Viability of the bacteria was determined periodically by titering the CFU/ml using spread plate techniques. Bacteria were serially diluted in 0.1% peptone, 0.005% TWEEN® 80 and then spread onto agar plates made from the media of deMan, Rogosa, and Sharpe (MRS). Colonies were enumerated after 48 hours of incubation at 37° C. in a 5% $CO_2$ atmosphere.

In order to test the effects of agitation on Lactobacillus BT 1386 viability, agitation was applied to a typical 8-liter batch contained in a 5-gallon tank. Agitation was provided by a stainless steel paddle having two 4-inch blades revolving at 63 r.p.m. Agitation was applied for either four minutes out of every ten minutes or for 0.25 minutes (15 seconds) out of every ten minutes. The results of the agitation tests are contained in Table 1 in the columns labeled "Agitation 4 min. of 10" and "Agitation 0.25 min. of 10".

In order to evaluate the effect of recirculation on the viability of *Lactobacillus acidophilus* BT 1386 cells in suspension, a typical 8-liter batch was recirculated within a 5-gallon tank. The tank was hydraulically connected to the inlet and outlet ports of a recirculation pump by nipples that prevented air from being introduced into the tank. The tank was covered. The recirculation pump was operated continuously to simulate constant recirculation conditions. At periodic intervals, the CFU per ml was determined as described above. The results are summarized in Table 1 under the heading "Constant Recirculation."

In order to simulate infrequent recirculation, another 8-liter batch was placed in a 5-gallon tank in a refrigerator. The recirculation pump was operated for one minute out of 24 hours. The CFU per ml was determined as described above for the "Constant Recirculation" at the same time intervals. The results are summarized in Table 1 under the heading "Infrequent Recirculation."

TABLE 1
EFFECT OF AGITATION AND RECIRCULATION ON VIABILITY OF
LACTOBACILLUS ACIDOPHILUS FROM FREEZE-DRIED CULTURES
Colony Forming Units per ml (CFU per ml)

|  | No Agitation | Agitation 4 min. of 10 | Agitation 0.25 min. of 10 | Constant Recirculation | Infrequent Recirculation |
|---|---|---|---|---|---|
| 0 hr. | $1.1 \times 10^9$ | $5.6 \times 10^8$ | $1.0 \times 10^9$ | $7.7 \times 10^8$ | $8.6 \times 10^8$ |
| 24 hr. | $6.3 \times 10^8$ | $6.4 \times 10^6$ | $1.5 \times 10^7$ | $9.8 \times 10^7$ | $4.1 \times 10^8$ |
| 48 hr. | $4.4 \times 10^8$ | $6.7 \times 10^3$ | $3.3 \times 10^4$ | — | $5.6 \times 10^8$ |
| 72 hr. | $2.3 \times 10^8$ | $3.3 \times 10^2$ | $1.0 \times 10^2$ | — | $5.2 \times 10^8$ |
| 96 hr. | $1.7 \times 10^8$ | $1.3 \times 10^1$ | $<1 \times 10^2$ | $1.3 \times 10^3$ | $2.8 \times 10^8$ |

EXAMPLE 2

To evaluate the effect of temperature on the viability of *Lactobacillus acidophilus*, the following procedure was followed. A suspension of the bacteria from a freeze-dried concentrate was prepared in a 100 ml flask. Immediately after the suspension was formed it was sampled for adenosine triphosphate (ATP) determination and colony forming units (CFU) per ml. The initial concentration of the suspension was approximately $10^9$ CFU per ml.

A sample of the suspension was placed under refrigeration at a temperature of about 40° F. Another sample was placed in an 80° F. environment. Each sample was analyzed for viability using an ATP luminometer at 6-, 24-, 48-, and 96-hour intervals. The results are summarized in Table 2 below.

TABLE 2
EFFECT OF WATER TEMPERATURE ON THE LONG-TERM VIABILITY OF LACTOBACCILUS ACIDOPHILUS FROM FREEZE-DRIED CULTURES
Colony Forming Units per ml (CFU per ml)

|  | 40° F. | 80° F. |
|---|---|---|
| 0 hr. | $1.4 \times 10^9$ | $1.4 \times 10^9$ |
| 6 hr. | $7.1 \times 10^8$ | $7.8 \times 10^8$ |
| 24 hr. | $6.4 \times 10^8$ | $7.9 \times 10^8$ |
| 48 hr. | $1.0 \times 10^9$ | $4.5 \times 10^8$ |
| 96 hr. | $4.6 \times 10^8$ | $1.2 \times 10^8$ |

EXAMPLE 3

The effect of time on the uniformity of a suspension of *Lactobacillus acidophilus* from a frozen concentrate and a suspension of *Lactobacillus acidophilus* from a lyophilized (freeze-dried) culture was observed according to the following procedure.

Seventy-five grams of a frozen bacterial concentrate containing approximately $5 \times 10^{12}$ CFU (approximately 10,000 doses) was added to 8,000 ml of tap water in a clear plastic tube having an inner diameter of approximately six inches and a height of approximately 24 inches. In an identical tube, 100 grams of a lyophilized culture containing approximately $5 \times 10^{12}$ CFU (approximately 10,000 doses) was added to 8,000 ml of tap water. In a third tube, identical to the first two tubes, a 1:10 dilution of the frozen concentrate mixture of bacteria was prepared by adding 800 mls of the frozen concentrate mix to 7,200 ml of tap water. No refrigeration was provided to the tubes.

The uniformity of the suspension was observed at 0, 15, and 30 minutes, 2, 24, 48 and 96 hours, and seven days after the suspensions were formed. The suspensions were also observed for sedimentation at the same time periods. The results are summarized in Table 3 below.

TABLE 3
EFFECT OF TIME ON UNIFORMITY OF SUSPENSION OF LACTOBACILLUS ACIDOPHILUS FROM FROZEN CULTURES AND LYOPHILIZED CULTURES

| Time | Lyophilized | Frozen | Diluted (1:10) Frozen |
|---|---|---|---|
| 0 | uniform, cloudy | uniform, cloudy | uniform, cloudy |
| 15 min. | clear layers at top, ¼ inch sediment | uniform, cloudy | uniform, cloudy |
| 30 min. | clear layers at top, ½ inch sediment | uniform, cloudy | uniform, cloudy |
| 2 hr. | 8 inch clear layer at top, 1 inch sediment | uniform, cloudy | uniform, cloudy |
| 24 hr. | 12 inch clear layer at top, 1.25 inch sediment | uniform, cloudy | uniform, cloudy |
| 48 hr. | clear throughout, one colony, slight mold growth, 1.5 inch sediment | uniform, cloudy | uniform, cloudy |
| 96 hr. | clear throughout, three colonies, some mold growth, 1.5 inch sediment | uniform, cloudy | uniform, cloudy |
| 7 days | clear throughout, extensive mold growth, 1.5 inch sediment | uniform, cloudy | uniform, cloudy |

Preliminary measurements indicate that the suspension derived from the frozen concentrate maintains a relatively stable pH over time, generally above about 6.5. The suspension derived from the freeze-dried concentrate exhibited a decrease in pH over time to a value of approximately 5.0. This would indicate that the reconstituted freeze-dried bacteria are metabolically active, i.e., producing lactic acid, which would be detrimental for feedlot applications because low pH creates an environment which reduces the lifetime of the bacteria. Also, at low pH such as that observed in the suspension derived from the freeze-dried concentrate, casein from the nonfat milk solids in the freeze-dried concentrate precipitates out of the suspension, adding to the sedimentation.

Although the present invention has been described in a specific form and as operating in a specific manner for the purposes of illustration, it is to be understood that the invention is not limited thereto. Various modifications will suggest themselves to those skilled in the art without departing from the spirit of this invention, the scope of which is set forth in the following claims.

The embodiments of the invention in which an exclusive property or privilege is claimed are defined as follows:

1. A method of dispensing live bacteria into animal feed or drinking water, the method consisting essentially of:

introducing a frozen concentrate of a liquid culture of live bacteria into an aqueous medium to prepare a suspension of the bacteria in the aqueous medium, said frozen concentrate being substantially free of cryoprotectants and carrier solids; and maintaining the suspension without agitation and without refrigeration for at least about 30 minutes, while dispensing aliquots of the suspension into animal feed or drinking water.

2. The method of claim 1, wherein the suspension is maintained without agitation and without refrigeration for at least about one hour.

3. The method of claim 1, wherein the suspension is maintained without agitation and without refrigeration for at least about 24 hours.

4. The method of claim 1, wherein the frozen concentrate has a solids content of less than about 100 grams per $5 \times 10^{12}$ CFU of bacteria.

5. The method of claim 1, wherein the live bacteria are microaerophilic bacteria.

6. The method of claim 1, wherein the live bacteria are anaerobic bacteria.

7. The method of claim 1, wherein the live bacteria are lactobacilli.

8. The method of claim 1, wherein the aliquots of the suspension are dispensed into animal feed or drinking water by mixing the aliquots with other feed additives which are collectively dispensed to the animal feed or drinking water.

9. The method of claim 1, wherein the aliquots of the suspension are dispensed into the animal feed or drinking water after being diluted with a liquid.

10. The method of claim 1, wherein the frozen concentrate contains about 7.5 grams of solids per approximately $5 \times 10^{12}$ colony forming units of live bacteria.

11. A method for dosing a population of domestic animals with live bacteria, the method consisting essentially of:

introducing a frozen concentrate of a liquid culture of a predetermined amount of live bacteria into a predetermined amount of an aqueous medium to prepare a suspension of the bacteria in the aqueous medium said frozen concentrate being substantially free of cryoprotectants and carrier solids; and maintaining the suspension without agitation and without refrigeration for at least about 30 minutes, while dispensing aliquots of the suspension into animal feed or drinking water.

12. The method of claim 11, wherein the suspension is maintained without agitation and without refrigeration for at least about one hour.

13. The method of claim 11, wherein the suspension is maintained without agitation and without refrigeration for at least about 24 hours.

14. The method of claim 11, wherein the aliquots of the suspension are dispensed into animal feed or drinking water by mixing with other feed additives, which are collectively dispensed to the animal feed or drinking water.

15. The method of claim 11, wherein the aliquots of the suspension are dispensed into animal feed or drinking water after being diluted with a liquid.

16. The method of claim 11, wherein the live bacteria comprise lactobacilli.

17. The method of claim 11, wherein the frozen concentrate contains about 7.5 grams of solids per approximately $5 \times 10^{12}$ colony forming units of live bacteria.

18. A method for maintaining live bacteria at an animal feedlot in a substantially viable condition for dispensing into animal feed or drinking water, the method consisting essentially of:

introducing a frozen concentrate of a liquid culture comprising live bacteria into an aqueous medium to prepare a suspension of the bacteria in the aqueous medium said frozen concentrate being substantially free of cryoprotectants and carrier solids; and maintaining the suspension without agitation and without refrigeration for at least about 30 minutes.

19. The method of claim 18, wherein the frozen concentrate contains about 7.5 grams of solids per approximately $5 \times 10^{12}$ colony forming units of live bacteria.

20. A method of dispensing live bacteria into animal feed or drinking water, the method consisting essentially of:

introducing a frozen concentrate of a liquid culture of live bacteria into an aqueous medium to prepare a suspension of the bacteria in the aqueous medium said frozen concentrate being substantially free of cryoprotectants and carrier solids; and maintaining the suspension without agitation for at least about 30 minutes, while dispensing aliquots of the suspension into animal feed or drinking water.

21. The method of claim 20, wherein the suspension is maintained without agitation for at least about one hour.

22. The method of claim 20, wherein the suspension is maintained without agitation for at least about 24 hours.

23. A method of dispensing live bacteria into animal feed or drinking water, the method consisting essentially of:

introducing a frozen concentrate of a liquid culture of live bacteria into an aqueous medium to prepare a suspension of the bacteria in the aqueous medium said frozen concentrate being substantially free of cryoprotectants and carrier solids; and maintaining the suspension without refrigeration for at least about 30 minutes, while dispensing aliquots of the suspension into animal feed or drinking water.

24. The method of claim 23, wherein the suspension is maintained without refrigeration for at least about one hour.

25. The method of claim 23, wherein the suspension is maintained without refrigeration for at least about 24 hours.

* * * * *

UNITED STATES PATENT AND TRADEMARK OFFICE
CERTIFICATE OF CORRECTION

PATENT NO. : 5,139,792

DATED : August 18, 1992

INVENTOR(S) : D.R. WARE et al.

It is certified that error appears in the above-identified patent and that said Letters Patent is hereby corrected as shown below:

| COLUMN | LINE | |
|---|---|---|
| 2 | 19 | "bacteria" should read —bacterial— |
| 11 | 43 | "LACTOBACCILUS" should read —LACTOBACILLUS— |
| 14 | 22 | "comprising" should read —of— |

Signed and Sealed this

Thirty-first Day of August, 1993

Attest:

BRUCE LEHMAN

Attesting Officer

Commissioner of Patents and Trademarks